(12) United States Patent
Goddard

(10) Patent No.: US 8,974,367 B2
(45) Date of Patent: Mar. 10, 2015

(54) COAXIAL DEVICE FOR DELIVERING AN IMPLANT TO A PATIENT'S PELVIC REGION

(75) Inventor: James Goddard, Pepperell, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1450 days.

(21) Appl. No.: 11/906,914

(22) Filed: Oct. 3, 2007

(65) Prior Publication Data

US 2008/0132753 A1 Jun. 5, 2008

Related U.S. Application Data

(60) Provisional application No. 60/849,405, filed on Oct. 3, 2006.

(51) Int. Cl.
*A61F 2/00* (2006.01)
*A61B 17/06* (2006.01)
*A61B 17/04* (2006.01)
*A61B 17/00* (2006.01)

(52) U.S. Cl.
CPC ....... *A61B 17/06109* (2013.01); *A61B 17/0485* (2013.01); *A61B 2017/00367* (2013.01); *A61B 2017/00805* (2013.01); *A61B 2017/06009* (2013.01); *A61B 2017/0608* (2013.01); *A61B 2017/06085* (2013.01); *A61B 2017/061* (2013.01)
USPC .......................................................... 600/37

(58) Field of Classification Search
USPC ......... 600/29–32, 37; 606/151, 113; 128/885, 128/899
See application file for complete search history.

(56) References Cited

U.S. PATENT DOCUMENTS

| | | | |
|---|---|---|---|
| 5,499,991 A | 3/1996 | Garman et al. | |
| 5,658,299 A | 8/1997 | Hart | |
| 6,858,026 B2 * | 2/2005 | Sliwa et al. | 606/28 |
| 7,878,969 B2 * | 2/2011 | Chu et al. | 600/30 |
| 2002/0099259 A1 * | 7/2002 | Anderson et al. | 600/29 |
| 2006/0058575 A1 | 3/2006 | Zaddem et al. | |
| 2006/0089524 A1 * | 4/2006 | Chu | 600/37 |
| 2006/0173468 A1 | 8/2006 | Simmon et al. | |
| 2007/0073098 A1 * | 3/2007 | Lenker et al. | 600/30 |

FOREIGN PATENT DOCUMENTS

| | | |
|---|---|---|
| WO | WO-9963893 | 12/1999 |
| WO | WO-2005077279 | 8/2005 |
| WO | WO-2005122954 | 12/2005 |
| WO | WO-2006081545 | 8/2006 |

* cited by examiner

*Primary Examiner* — Christine Matthews

(57) ABSTRACT

Systems and methods for implanting a surgical sling in a patient by a transobturator approach are disclosed. A sling delivery device couplable to a sling assembly with the surgical sling includes a guide tube and an extendible shaft section movable inside the guide tube. At least a portion of the shaft may be made of a shape memory material and can, when extended, assume a shape different from the shape of the guide tube in which the shaft is housed. This allows the extended shaft to navigate along a path that tracks close to bone structures, in particular the ischiopubic ramus, and prevents damage to surrounding tissue.

20 Claims, 7 Drawing Sheets

COAXIAL DEVICE FOR DELIVERING AN IMPLANT TO A PATIENT'S PELVIC REGION

CROSS REFERENCE TO RELATED APPLICATIONS

This application claims the benefit of and priority to U.S. Provisional Patent Application Ser. No. 60/849,405, filed on Oct. 3, 2006, which is hereby incorporated by reference in its entirety.

BACKGROUND

Urinary incontinence ("UI") occurs in both men and women. Various types of incontinence are caused by different conditions and call for different treatments. For example, stress urinary incontinence ("SUI") is known to be caused by at least two conditions, intrinsic sphincter deficiency ("ISD") and hypermobility. Moreover, UI is often caused or exacerbated by pelvic floor disorders. According to some studies, about 1 out of 11 women need surgery for a pelvic floor disorder during her lifetime. The pelvic floor generally includes muscles, ligaments, and tissues that collectively act to support anatomical structures of the pelvic region, including the uterus, the rectum, the bladder, and the vagina. Pelvic floor disorders include vaginal prolapse, vaginal hernia, cystocele, rectocele, and enterocele. Such disorders are characterized in that the muscles, ligaments and/or tissues are damaged, stretched, or otherwise weakened, which causes the pelvic anatomical structures to fall or shift and protrude into each other or other anatomical structures. Often, treatments of stress incontinence are made without treating the pelvic floor disorders at all, potentially leading to an early recurrence of the pelvic floor disorder.

One way to treat UI, both in men and women, is to place a surgical sling or suture in the periurethral tissue such as under the bladder, bladder neck or the urethra to provide a support platform. Placement of the sling helps to address UI by limiting mobility of the bladder neck or limits the endopelvis fascia drop while providing compression under event stress to improve urinary function. The sling may also be configured to address pelvic floor disorders by being positioned under a prolapsed organ in the pelvic region.

Current support slings are typically affixed using a bone anchoring method or a suture applied to the buttock, groin, or other area in the patient's pelvic region. Alternatively, an operator uses an anchorless approach to stabilize the urethra with a sling by placing the sling in the periurethral tissue and relying on tissue compression and eventual tissue in-growth to secure the sling in position.

Various transvaginal, suprapubic, and trans-obturator approaches have been used for sling placement. In the case of trans-obturator approaches, current approaches use a needle delivery device having a fixed radius of curvature. Often such technique is performed in an "inside-out" fashion that involves inserting a delivery device and support sling through a vaginal incision in a patient, then tunneling the sling through the patient's obturator foramen and then through a groin incision. The tissue in the posterior region of the obturator foramen includes sensitive vascular and nerve tissues which may be punctured by the device as it tunnels through the obturator foramen. Alternative transobturator approaches include an "outside-in" approach in which the needle is tunneled from a groin incision to a vaginal incision and associated with the implant. The implant is then drawn back through the passage and out the groin incision. It would be desirable to provide a sling delivery device with a geometry that allows the shaft of the delivery device to track closely around a bodily structure, such as the ischiopubic ramus, during the advance of the delivery device through the tissue to allow the device to by-pass sensitive posterior obturator foramen tissues. Accordingly, devices, systems, and methods are desirable that can track a curved path with varying radius for positioning a mid-urethral sling to treat urinary incontinence, while minimizing the risk of injury to the patient.

SUMMARY

The invention addresses deficiencies of the prior art by, in one embodiment, providing delivery devices, systems, and methods for facilitating delivery of an implant to an anatomical site by way of the obturator foramen. In particular, the invention provides delivery devices, systems, and methods for placing an implant, e.g., a sling for treating UI (including SUI) or pelvic floor disorder. In one embodiment, it facilitates placement by a trans-obturator approach. In one aspect, the invention provides a delivery device for delivering a supportive sling through an anterior vaginal incision and through the obturator foramen of the patient. In one embodiment, the invention provides a delivery device for positioning a supportive sling between a vaginal incision and a patient's obturator foramen without penetrating the obturator foramen. In one embodiment, the delivery device includes a curved guide tube, and an extendible/retractable shaft extending from a distal end of the guide tube. The guide tube may include one or more substantially straight sections and/or one or more curved sections. The device may also include a handle connected to the guide tube. The guide tube and the handle can be substantially in the same plane. Preferably, the section(s) of the shaft that extend into the patient's body are located substantially in a single plane.

According to one aspect of the invention, a sling delivery device includes a guide tube with a proximal end and a distal end and having a first radius of curvature, a handle joined to the proximate end of the guide tube, a shaft slidingly interfitted in the guide tube with a proximal end and a distal end, and an actuator (e.g., a slider) secured on the handle and operatively connected to the proximal end of the shaft for extending the shaft from the distal end of the guide tube and retracting the shaft into the distal end of the guide tube. At least the portion of the shaft extending from the guide tube is made of a shape memory material and can assume a second radius of curvature different from the first radius of curvature of the guide tube.

According to another aspect of the invention, a sling delivery assembly includes a delivery device with a guide tube having a proximal end and a distal end, wherein the distal end of the guide tube has a first radius of curvature. The delivery device also includes a shaft slidingly interfitted in the guide tube and also having a proximal end and a distal end. The distal end of the shaft has a radius of curvature substantially identical to the first radius of curvature while inside the guide tube, and is capable of assuming a second radius of curvature different from the first radius of curvature when protruding from the distal end of the guide tube. A first connector is attached to or integrally formed with the distal end of the shaft. The delivery assembly further includes a sling assembly having a proximal end and a distal end, with a second connector attached to or integrally formed with the distal end of the sling assembly and adapted for engagement with the first connector.

According to yet another aspect of the invention, a method of treating urinary incontinence includes the steps of inserting a delivery device coupled to a sling assembly with the surgical sling through a vaginal incision point of a patient, advancing the delivery device to the transobturator foramen, extending a shaft portion from a distal end of the delivery device to navigate around a bodily structure, with the extended shaft portion assuming a curvature different from a curvature of the distal end of the delivery device, and retracting the extended shaft portion after placement of the surgical sling, with the retracted shaft portion conforming again to the curvature of the distal end of the delivery device.

In one embodiment, the sling delivery device may include a connector attached to or integrally formed with the distal end of the shaft and adapted to attach to a sling assembly. Since shape memory materials change their shape, inter alia, due to a temperature-induced phase transition, the shaft may include a lumen and a heating or cooling element disposed in the lumen in at least the portion of the shaft made of the shape memory material. The heating element can be energized to increase the temperature of the shape memory material above a phase transition temperature of the material when at least the portion of the shaft made of the shape memory material is extended to protrude from the distal end of the guide tube. Alternatively or in addition, the cooling element can be energized to decrease the temperature of the shape memory material below a phase transition temperature of the material when at least the portion of the shaft made of the shape memory material is retracted inside the distal end of the guide tube. The shape memory material may be a nickel titanium alloy, such as Nitinol, which exhibits excellent biocompatibility. The phase transition temperature of the shape memory material can be adjusted, for example, by adjusting the composition or by mechanical or heat treatment, to be around the body temperature of a mammal, e.g., a human patient.

The second radius of curvature of the extended portion of the shaft may be smaller than the first radius of curvature of the guide tube. However, the extended portion of the shaft may be designed to have any suitable shape, including complex shapes, with the extended portion assuming the complex shape when at a temperature above the phase transition temperature of the shape memory material.

The extendible shaft may have a tip, such as a dilator tip and/or a tissue dissector, at the distal end capable of piercing tissue. Alternatively or in addition, the connector on the sling assembly which is couplable to the distal end of the shaft may also include a dilator.

Additional features and advantages of the invention will be apparent from the following description of preferred embodiments.

BRIEF DESCRIPTION OF THE FIGURES

The following figures depict certain illustrative embodiments of the invention in which like reference numerals refer to like elements. These depicted embodiments may not be drawn to scale and are to be understood as illustrative of the invention and not as limiting in any way.

DESCRIPTION OF ILLUSTRATIVE EMBODIMENTS

Figure 1:
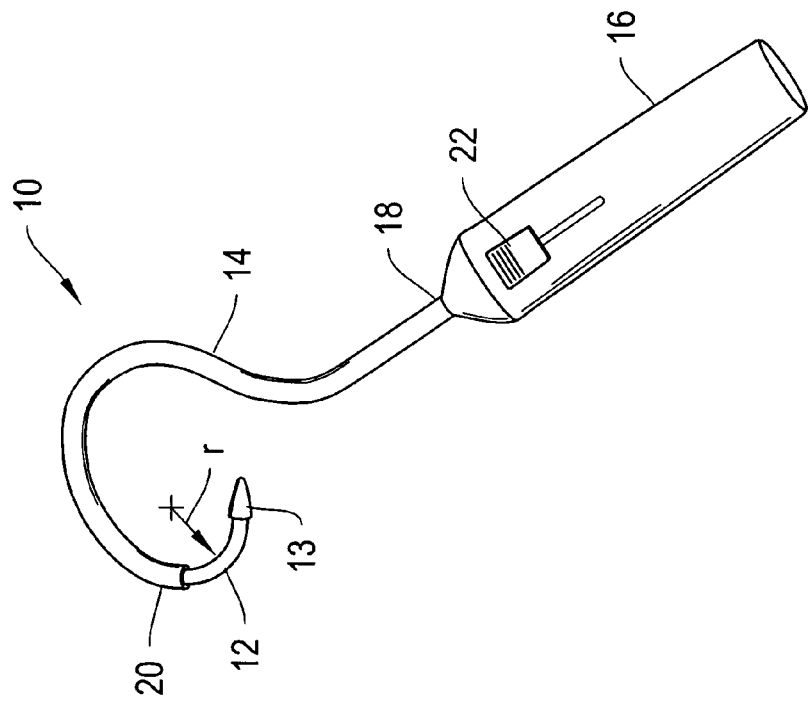
FIG. 1 is a perspective view of a delivery device adapted to implant a sling within the pelvic region of a patient, with an interior shaft in a retracted position inside a guide.

As described in summary above, the invention, in certain illustrative embodiments, relates to systems and methods for delivering and placing a medical implant at an anatomical site in the body of a mammal. In particular, in various illustrative examples, the invention provides delivery devices, systems, and methods for placing an implant, e.g., a sling for treating UI (including SUI) or pelvic floor disorders, by a trans-obturator approach. In one aspect, the implant includes a supportive sling and is delivered to the periurethral tissue of a patient via the obturator foramen. The patient may be either a female patient or a male patient.

As described below in further detail, the illustrative delivery devices include a guide tube. The guide tube may include one or more substantially straight sections and/or one or more curved sections. The cross-section of the guide tube may have a constant shape and size, or its shape and/or size may vary along its length. The cross-section of the guide tube may assume any suitable shape, for example, circular, semi-circular, oval, triangular, or rectangular. A handle may also be included, and the guide tube may be configured to extend from a distal end of the handle.

Preferably, the guide tube is formed from a metal or a polymeric material. Examples of suitable metals include, but are not limited to, stainless steel, titanium, and alloys such as a nickel titanium alloy having the trade name Nitinol. Suitable polymers, which can be used as a coating on a metal to form the guide tube, include but are not limited to, plastics such as polytetrafluoroethylene (PTFE). In some configurations, the guide tube is rigid. However, in other configurations, the guide tube has some flexibility, and can be described as semi-rigid.

A shaft is moveably disposed inside the guide tube and may have a conical tip at the distal end. The conical tip is configured for percutaneous dissection and advancement through tissue. The tip may be blunt or sharp. A blunt tip provides resistance to unintended penetration through tissue or organ, such as the bladder. The shaft may be solid or hollow. If the shaft is at least partly hollow, it may include a lumen adapted to receive a heating/cooling element. In other embodiments, the distal end includes an enlarged, flared portion to dilate tissue beyond the nominal diameter of the shaft.

In one illustrative embodiment, the tissue contacting surface of the guide tube and/or the shaft is smooth and may be coated with one or more drugs such as anesthetic, anti-inflammatory, coagulating, anticoagulating, antibiotic, or antimicrobial agents. The drug may be delivered to the patient's tissue while the shaft is in contact with the tissue. The surface of the shaft may be coated with a light-absorbing coating to reduce glare, for example, under a cystoscope. The coating may be a polymer, such as Teflon, or other suitable material, and may be colored to aid in detection. The surface of the guide tube and/or the shaft may be painted so that one can easily distinguish it from surrounding tissue and fluid under a cystoscope. In other illustrative embodiments, the guide tube is textured, for example, by stippling, to provide increased traction relative to a gloved hand of a medical operator.

Referring now to FIG. 1, a delivery device 10 is depicted having a guide tube 14, a handle 16, and a shaft 12 movable within the guide tube 14. The shaft 12 has a needle-shaped or blunt tip 13. The proximal end 18 of the guide tube 14 is attached to the distal part of the handle 16. Such attachment may be through any suitable approach, including brazing, threading or other means. In certain implementations, the handle 16 is provided with knurling or other surface texturing to produce a high friction gripping surface. The guide tube 14 has a proximal end 18 and a distal end 20, and can also function as a dilator. A tubular member or wall of the guide tube 14 forms a lumen that allows the shaft 12 to slideably move inside the guide tube 14. The guide tube 14 is made of stainless steel or plastic, or of another suitable biocompatible material, such as Nitinol.

The handle 16 includes an actuator 22 operatively connected to the proximal end of the shaft 12. The connection between the actuator 22 and the shaft 12 may be permanent or reversible (removable and reusable). The illustrative actuator 22 operates the shaft 12 through a mechanical interconnection or linkage (not shown). However, in alternative embodiments, the actuator 22 may operate through electrical, chemical, magnetic, piezoelectric, hydraulic, pneumatic, or other suitable mechanisms, separately or in combination. The dissection tip 13 can be extended from and retracted toward or into the lumen at the distal end 20 of guide tube 14 by manipulating the actuator 22, which may be implemented as a lever or slider, or another suitable element disposed on the handle. The actuator 22 may be biased to a rest position, for example, a position where the shaft 12 is retracted in guide tube 14, by a suitable spring mechanism (not shown), which can be disposed inside the handle 16. This would allow an operator to retract the shaft 12 into the guide tube 14 simply by releasing the actuator 22 after completion of a sling implantation procedure. In FIG. 1, the actuator 22 is shown at its proximal position, so that the distal end of the shaft 12 and hence also the tip 13 is withdrawn toward or into the distal end of guide tube 14. Conversely, in FIG. 2, the actuator 22 is at its distal position, so that the tip 13 and the distal portion of shaft 12 protrude from the distal end 20 of the guide tube, for example, by about 0.25 to about 1 inch. In both the retracted (FIG. 1) and the extended position (FIG. 2) the tip 13 is capable of piercing and/or dissecting tissue and membranes.

The exemplary guide tube 14 in the depicted illustrative embodiment includes a distal portion having approximately the shape of a partial circle with a radius R, and a length of between about 6 inches (15 cm) to about 10 inches (25 cm). However, the dimensions and shape of the guide tube and the associated shaft may have any other suitable shape, such as multiple curved and straight sections, depending on anatomical considerations and the type of procedure in which it is intended to be used. In the exemplary embodiment depicted in FIG. 2, the extended shaft 12 is designed to have a radius r that is smaller than the radius R of the adjacent portion of guide tube 14. However, in alternate embodiments, the radius r is greater than the radius R, while in other-embodiments the shaft 12 has a more complex shape when extended out of the guide tube 14. In certain implementations, the shaft 12 has a section with a pre-shaped radius r that takes the shape of the tube 14 having radius R when forced into the tube 14 but reverts to radius r when expelled from the tube. In alternative configurations, the desired shape is impressed on the memory metal section of the shaft 12 and is recovered by increasing the temperature of the shaft 12 above the phase transition temperature of the shape memory material. In one approach, the shaft 12 is constructed of a flexible, springy material having an inherent radius r, which is bent when inside the guide tube 14 to assume the larger radius R. However, in preferred approaches, the shaft 12 is also able to pierce tissue and is therefore rigid.

In certain embodiments, the desired change in radius of the shaft 12 is achieved by using a suitable shape memory material, such as Nickel Titanium (NiTi or Nitinol) in the shaft 12 construction. The shape memory material Nitinol undergoes a phase transformation in its crystal structure when cooled from the stronger, high temperature form (austenite) to the weaker, low temperature form (martensite). Nitinol contains a nearly equal mixture of nickel (about 55 wt. %) and titanium. Other elements may be added to adjust or "tune" the material properties. When a shape memory material is in its martensitic form, it is easily deformed to a new shape. However, when the alloy is heated through its transformation temperature, it reverts to austenite and recovers its previous shape with great force. This process is known as memory shaping.

The temperature at which the alloy reverts to its high temperature form when heated may be adjusted by slight changes in alloy composition and through heat treatment. In certain NiTi alloys, for example, the phase transition temperature may be changed from above +100° C. to below −100° C. by varying the relative concentrations of the alloy components. The shape recovery process occurs over a range of just a few degrees and the start or finish of the transformation can be controlled to within a degree or two if necessary. The austenitic phase of NiTi has a yield strength of 35,000 to 100,000 psi, whereas the martensitic phase has a much lower yield strength of 10,000 to 20,000 psi. The unique properties of NiTi have provided the enabling technology for many groundbreaking applications in the medical and dental industries. These applications have included surgical tools and permanent implants, including implants within the bloodstream. The excellent biocompatibility, high corrosion resistance, and excellent cytocompatibility of NiTi have made these unique applications possible. The nickel in NiTi is chemically joined to the titanium in a strong intermetallic bond, so the risk of reaction in patients with nickel sensitivity is extremely low. Being constructed at least in part of shape memory material, the extendible portion of shaft 12 may be designed to have any desirable shape that has been heretofore attainable only by using delivery devices with a complex shape.

The shape memory delivery device described above may be used to deliver and place a suitable implant, such as a sling (e.g., a knitted mesh), or a sling assembly, at a desired anatomical site in a patient's body. Additionally, any suitable mechanism may be employed to associate the sling assembly with the shaft of the delivery device. In a preferred embodiment, the sling assembly does not affix, attach, connect or join with the shaft of the delivery device. Instead it may hook or slide onto the delivery device, preferably in a releasable fashion.

Figure 3A:
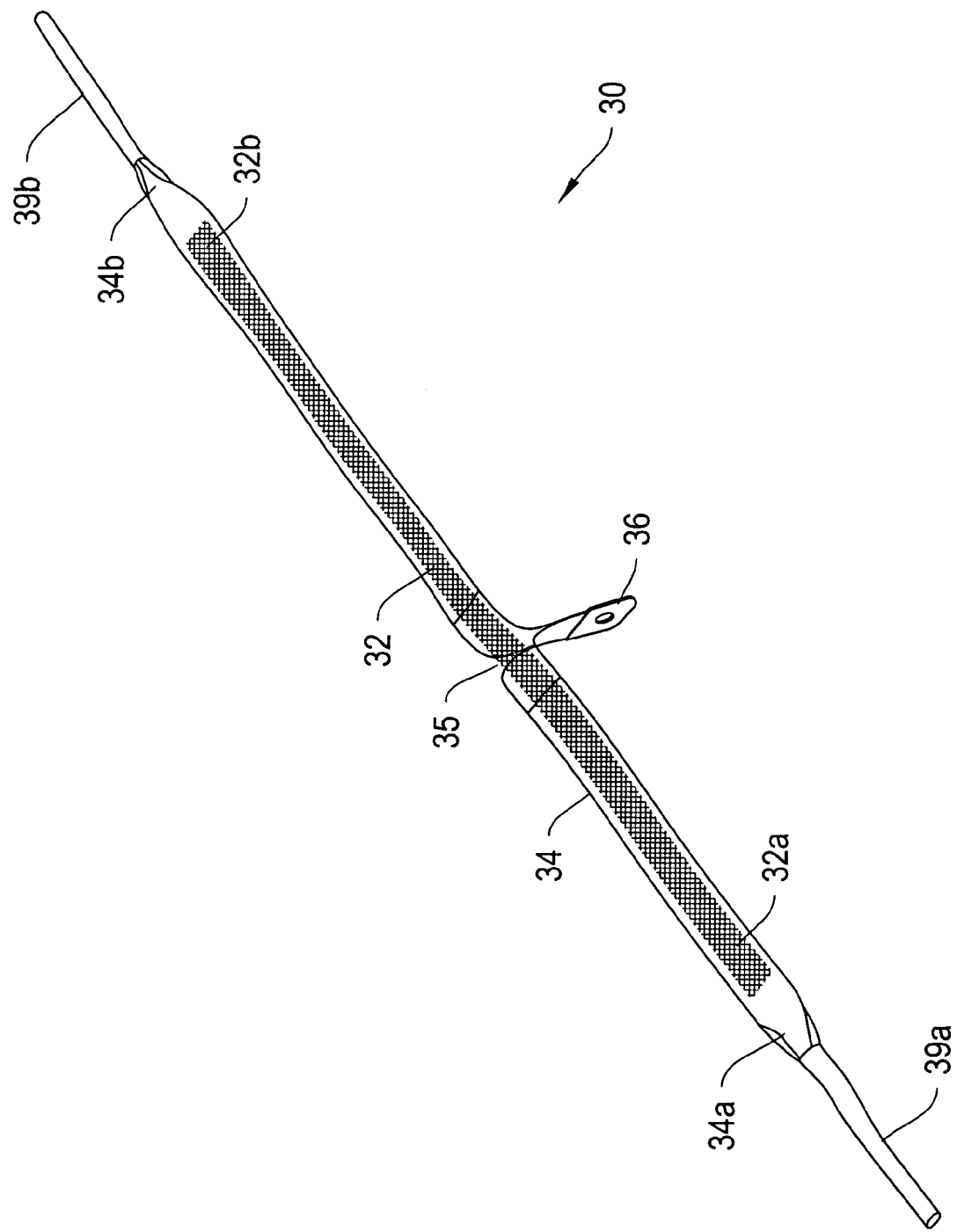
FIG. 3A depicts a sling assembly with dilator tubes.

FIG. 3A depicts an exemplary sling assembly 30 adapted to be inserted into a patient by use of the delivery device 10. The illustrated sling assembly 30 includes a sling 32 formed from a knitted mesh and a flexible sleeve 34 formed from a flexible polymer plastic. The length of the sling 32 is shorter than the length of the sleeve 34, and the sling 32 does not connect to the sleeve 34 or anything else. The sling assembly 30 inhibits the medical operator from gripping the free ends of the sling 32 and inadvertently tensioning the sling 32. This feature may be further enhanced by making the sling 32 long enough to support the urethra but not long enough to expose the ends of the sling outside the body. This may have the advantage of preventing infection caused by the exposure of the sling external to the body. By way of example, an illustrative sleeve 34 may be longer than the sling 32 by approximately about 1 cm to 10 cm, or even 30 cm. In particular, in transobturator procedures, the sling 32 may be configured to be long enough to extend to, or through, both of a patient's obturator foramen but not long enough to extend outside of the body. In other embodiments, the sling 32 may be configured in length to extend outside of the body, when placed, and the ends then trimmed to length by the physician to a point just under the skin. In certain implementations, the sling 32 is configured to have a substantial width that allows it to support a prolapsed organ, such as a bladder, urethra, or other organ located in the pelvic region, and such a sling may have one or more support legs that are adapted to extend to the vicinity of or be placed within the patient's obturator foramen membrane. In certain implementations, support legs are provided in a length that allows the legs to extend to and anchor in an anatomical location in front of the obturator membrane without penetrating the obturator membrane. Exemplary slings for supporting pelvic organ prolapse are disclosed in U.S. patent application Ser. No. 11/400,111, filed Apr. 6, 2006 and entitled "Systems, Devices and Methods for Treating Pelvic Floor Disorders" and Ser. No. 11/399,913, filed Apr. 6, 2006 and entitled "Systems, Devices and Methods for Suburethral Support," the contents of each of which are incorporated by reference herein in their entirety.

As depicted in FIG. 3A, in certain implementations the sling 32 is positioned within a sleeve 34. Each end of the sleeve 34 connects to a dilator tube 39a or 39b which is connected to a respective portion of end 34a and 34b, of the sleeve 34. The dilator tubes 39a and/or 39b may taper in a direction toward or away from the midpoint of the sling assembly 30 depending on into which end of the guide tube a delivery device shaft is to be inserted. The dilator tubes may be affixed to the sling assembly 30 ends by any suitable mechanism, including gluing, heat bonding, shrink tubing or the like.

In certain embodiments, the dilator tubes 39a and 39b are designed to slide onto the guide tube 14 of a delivery device 10, and preferably the inner diameter of the dilator tubes 39a and 39b is larger than the diameter of the curved shaft 12 or the diameter of at least one section of the shaft, e.g., the distal end of the shaft. The dilator tubes 39a and 39b may be constructed so that the tip 13 of the shaft 12 entrains the dilator tubes 39a and 39b and carries them with it when the shaft 12 is extended from the guide tube 14. (See also FIGS. 4 and 5). In the depicted embodiment, the dilator tubes 39a and 39b are bonded to the sleeve 34, such that the dilator tubes 39a and 39b secure the respective ends 34a and 34b of the sleeve 34 of the sling assembly to the tip 13 of the delivery device 10 and facilitate expansion of tissue along a respective path during sling assembly placement. In other embodiments, the dilator tubes may include hooks or loops configured to engage in mating structures, such as L-slots, formed onto tip 13. As described below, in other embodiments, the tubes 39a and 39b are soft tissue anchors that are bonded to the sling and adapted to anchor the sling to the patient's tissues and remain in place after placement of the sling. In certain embodiments, the tubes 39a and 39b are made of a biodegradable material.

The sleeve 34 may be made, for example, from one or more absorbent materials, such as a sponge-like material, that can optionally be pre-soaked in a drug solution, for example, in an anesthetic, anti-inflammatory, coagulating, anticoagulating, or antibiotic solution. In another embodiment, the sleeve 34 may be made from a non-wettable material, such as polypropylene, polyethylene, polyester, polytetrafluoroethylene (available from DuPont Corporation, Wilmington, Del., under the trademark TEFLON™, TYVEK™, MYLAR™), or co-polymers thereof. The non-wettable materials can also be pretreated with a therapeutically effective drug coating. The sleeve 34 is preferably transparent so that an operator will be able to see the implantable sling 32 inside the sleeve 34.

Figure 3B:
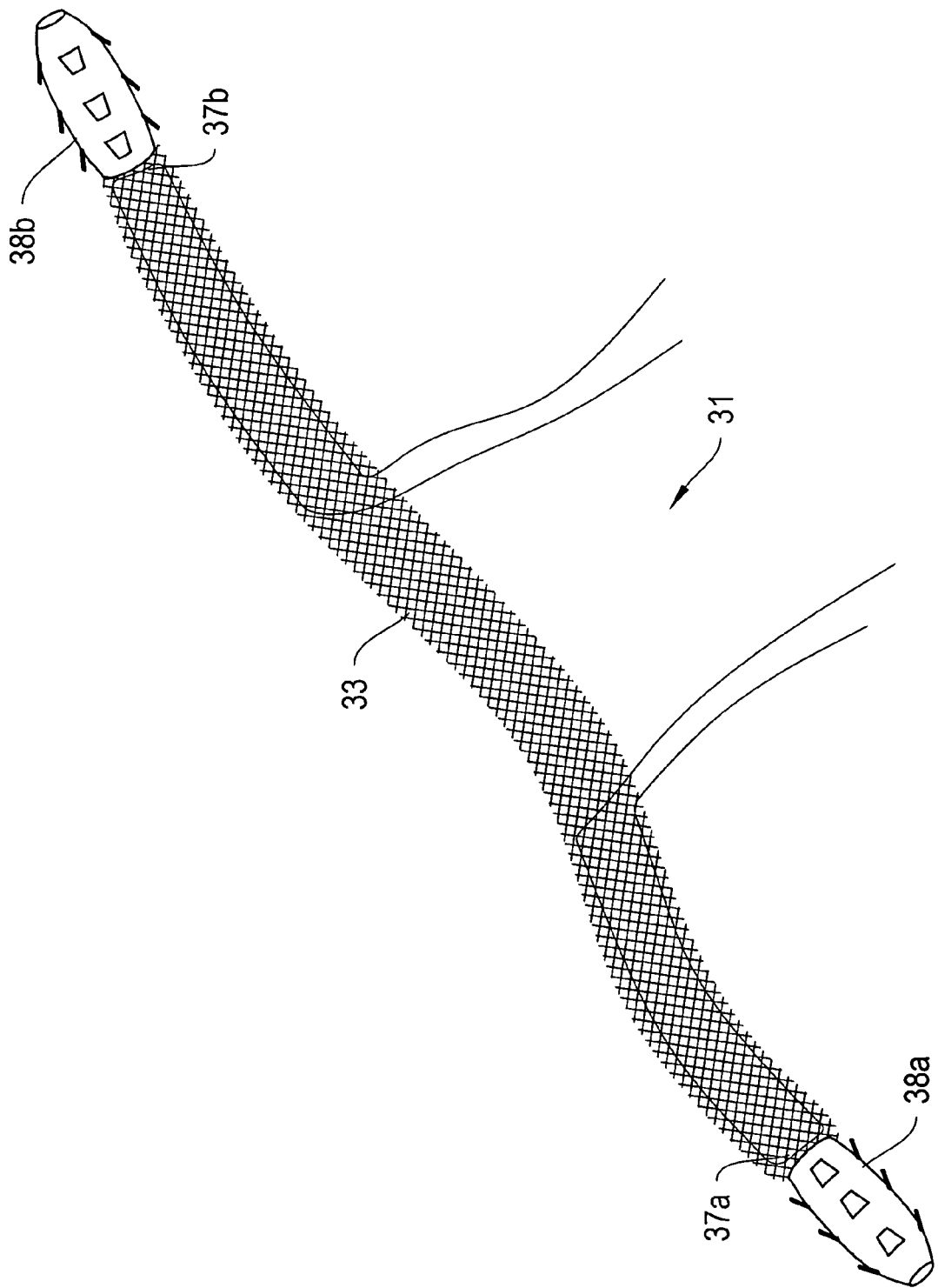
FIG. 3B depicts a sling assembly with soft tissue anchors.

In certain embodiments depicted in FIG. 3B, the sling assembly does not include a sleeve. Instead, the ends of the sling 33 include tissue anchors 38A and 38B, preferably provided with suitably shaped barbs that anchor the sling 33 in the tissue near the obturator foramen. Exemplary tissue anchors are disclosed, for example, in U.S. patent application Ser. No. 11/152,898, the entire contents of which are incorporated herein by reference. The sling 33 may be attached to tissue anchors 38A and 38B at locations 37A and 37B in a number of ways, for example, by clamping, heat fusion or other type of material connection. The tissue anchors 38A and 38B may include suitable coupling structures, such as coaxially aligned openings or blind holes for engagement with the tip 13 of shaft 12 of delivery device 10. However, as described below, the sling 33 may also be anchored in the tissue without the attached tissue anchors, for example, by providing a "tanged" section at the ends of sling 33 which anchor the sling 33 and/or encourage tissue growth. Anchoring the sling in the soft tissue obviates the need for an additional ishiopubic incisions and sutures.

In certain embodiments, a sling that may be used with the exemplary device, such as sling 32, has a length of about 10 to about 45 cm and a width of about 1 cm to about 3 cm, though the length and width of the sling can be adapted to the body part of the patient that requires support. The sling 32 may be rectangular or have another suitable shape. The sling 32 may have a uniform thickness over the entire length and/or width of the sling. Alternatively, the thickness can be suitably varied at one or more locations. The thickness of the sling material may range from about 0.02 to about 0.10 cm. In one embodiment, the sling is a strip of mesh with any of a number and/or configurations of knits, weaves, or braids. The sling 32, including both free ends, does not connect to the sleeve 34 or anything else. This feature enables a medical operator to pull on the ends of the sleeve 34 during sling assembly placement, for example, via the dilator tubes 39a and 39b and/or any of the delivery devices to be used for placement, without risk of stretching, curling or otherwise deforming the sling 32.

The sling 32 may be fabricated from any of a number of biocompatible materials, such as nylon, polyethylene, polyester, polypropylene, fluoropolymers, copolymers thereof, combinations thereof, or other suitable synthetic material(s). The material may be, for example, a synthetic material that is absorbable by the patient's body. Suitable absorbable synthetic materials can include polyglycolic acid, polylactic acid, and other suitable absorbable synthetic materials. Alternatively, the material for the sling may be derived from mammalian tissue(s) or a combination of mammalian tissue(s) and synthetic material(s). The sling material may be fabricated from one or more yarns, which yarns may be made from one or more materials. The sling may incorporate or be coated with one or more agents to provide a therapeutic effect, for example, to reduce discomfort, to reduce the chance of infection and/or to promote tissue growth.

In one embodiment, the edge regions of the sling 32 can be configured differently depending on their intended placement in the body of the patient. For example, a midsection of the sling is typically located to support an anatomical site, such as a mid-urethral or bladder neck location in the periurethral tissue. In one illustrative embodiment, the midsection of the sling has smooth or rounded edges, hereinafter also referred to as "non-tanged" or "de-tanged." According to a further illustrative embodiment, other sections of the sling may include tangs (e.g., sharp projections or frayed edges). The tangs are generally useful for anchoring the sling 32 and/or encouraging tissue growth into the sling. Anchoring the sling in this manner generally obviates the need for additional sutures to hold the sling in place. Examples of suitable tanged configurations are disclosed in U.S. patent application Ser. No. 11/400,111, filed Apr. 6, 2006 and entitled "Systems, Devices and Methods for Treating Pelvic Floor Disorders" and Ser. No. 11/399,913, filed Apr. 6, 2006 and entitled "Systems, Devices and Methods for Suburethral Support."

The tanged and non-tanged edges of sling can be formed in any suitable way. For example, the sling can be cut from a woven sheet, in which case the edges would be initially tanged along the entire length of the sling. One or more non-tanged sections may be formed by any process that smoothes, rounds or removes the sharp edges of the tangs. For example, the tangs may be heat-smoothed by burning or melting the tangs. In one embodiment, the non-tanged section has a length of about 1 to about 5 cm, preferably about 2 to about 2.5 cm, on either or both sides of the center line of the sling. Providing one or more non-tanged sections, which may be in close proximity to a sensitive anatomical site in the patient, can enhance the comfort level of the patient and reduce the potential for the edges of the tangs to erode or irritate the urethra. Alternatively, the sling can be produced from a woven tape having the approximate finished width of the sling. The smooth sides of the tape can then be trimmed off to produce the tanged sections.

An opening 35 in the sleeve 34 can be formed at a midpoint of a top portion of the sleeve 34 to expose the entire width of the sling 32. As indicated in FIG. 3, in certain implementations a tabbed spacer 36 is used with the sleeve 34 and located at a midpoint of a bottom side of the sleeve 34 so as to enclose a looped portion of the bottom side of the sleeve 34. The tabbed spacer 36 can be used during implantation as a visual aid to placement of the sling 32. The tabbed spacer 36 also engages the looped portion of the bottom side of the sleeve 34 and prohibits the sleeve 34 from sliding off, or otherwise being removed from, the sling 32 during sling assembly placement. Preferably, the tabbed spacer 36 is cut to enable the sleeve 34 to slide off the sling 32. This feature ensures that the sleeve 34 cannot be removed simply by applying a pulling force, such as that applied to the sling assembly ends by a medical operator during sling assembly placement. After the sling assembly is positioned within the patient, a cut is made through the center of the tabbed spacer 36, and thus through the looped portion of the bottom side of the sleeve 34. The sleeve 34 is then slid off of the sling 32, out of the body of the patient, and discarded. In embodiments where the dilator tubes 39a and 39b are bonded to the sleeve 34, the tubes are clipped from the sleeve prior to removing the sleeve from the sling after the sling placement. In embodiments where the tubes 39a and 39b are soft tissue anchors, they remain in place after placement of the sling.

Without limitation, exemplary sling assembly configurations and/or connectors that may be operable with illustrative embodiments of the invention are found in the patents and patent applications cited herein, and in U.S. patent application Ser. No. 10/641,170; U.S. patent application Ser. No. 10/641,192; U.S. provisional Patent Application Ser. No. 60/495,439, U.S. patent application Ser. No. 10/640,838; U.S. provisional Patent Application Ser. No. 60/403,555; U.S. provisional Patent Application Ser. No. 60/465,722; U.S. patent application Ser. No. 10/460,112; U.S. patent application Ser. No. 09/096,983, and U.S. patent application Ser. No. 10/957,926, the entire contents of all of which are incorporated herein by reference.

Figure 2:
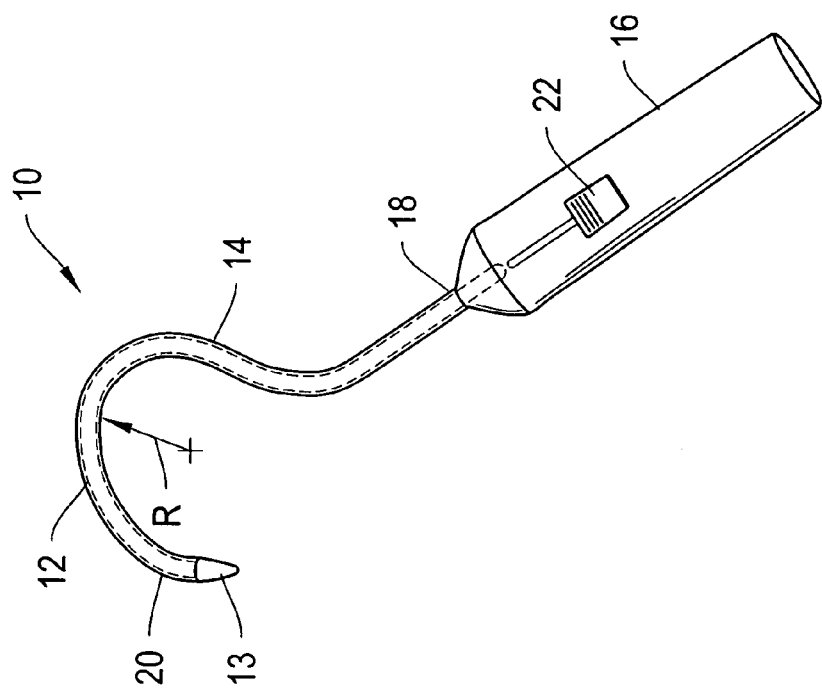
FIG. 2 is another perspective view the delivery device of FIG. 1, with the interior shaft in an extended position.
Figure 4:
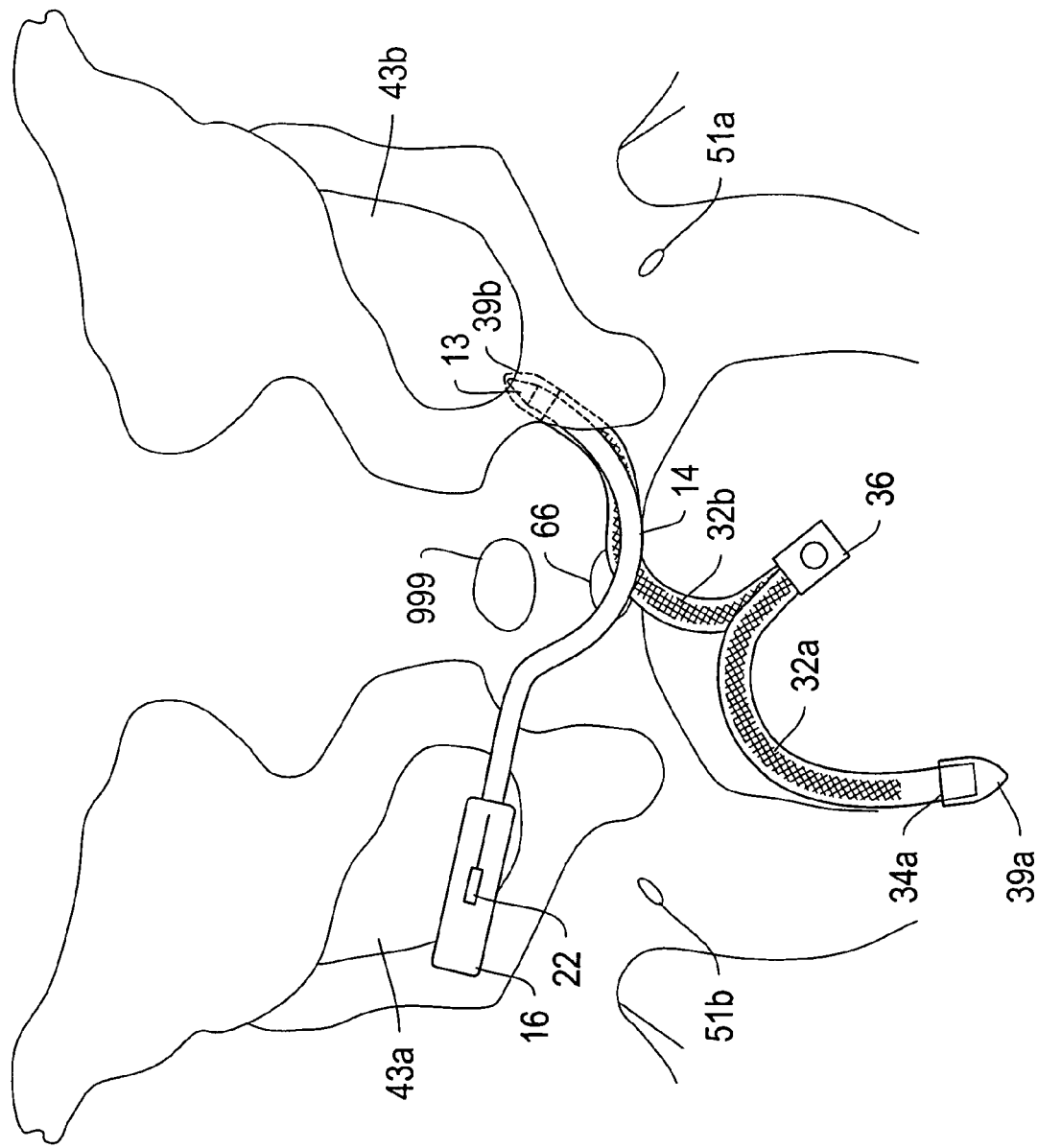
FIG. 4 depicts an illustrative trans-obturator approach with the delivery device of FIG. 1 inserted in a vaginal incision.

FIG. 4 depicts an illustrative example of associating the dilator tubes 39a and 39b with the shaft 12 of a delivery device 10 of FIGS. 1 and 2 for placing a sling underneath the urethra 999. As depicted in FIG. 4, according to one approach, the conical tip 13 of the shaft 12, while still retracted toward or into guide tube 14, is inserted into the dilator tube 39b that is bonded to the sleeve end 34b or to the sling assembly 30 (FIG. 3). Preferably, the dilator tube 39b slides easily on and off the shaft 12 of the delivery device 10. In alternative embodiments, not shown, the sling assembly ends include receptacle connectors or mating structures, for forming a secure attachment between the sling assembly end and the distal end of the delivery device shaft. These and other embodiments are disclosed, for example, in commonly assigned U.S. patent application Ser. No. 10/956,926, the contents of which are included herein by reference in their entirety.

Figure 5:
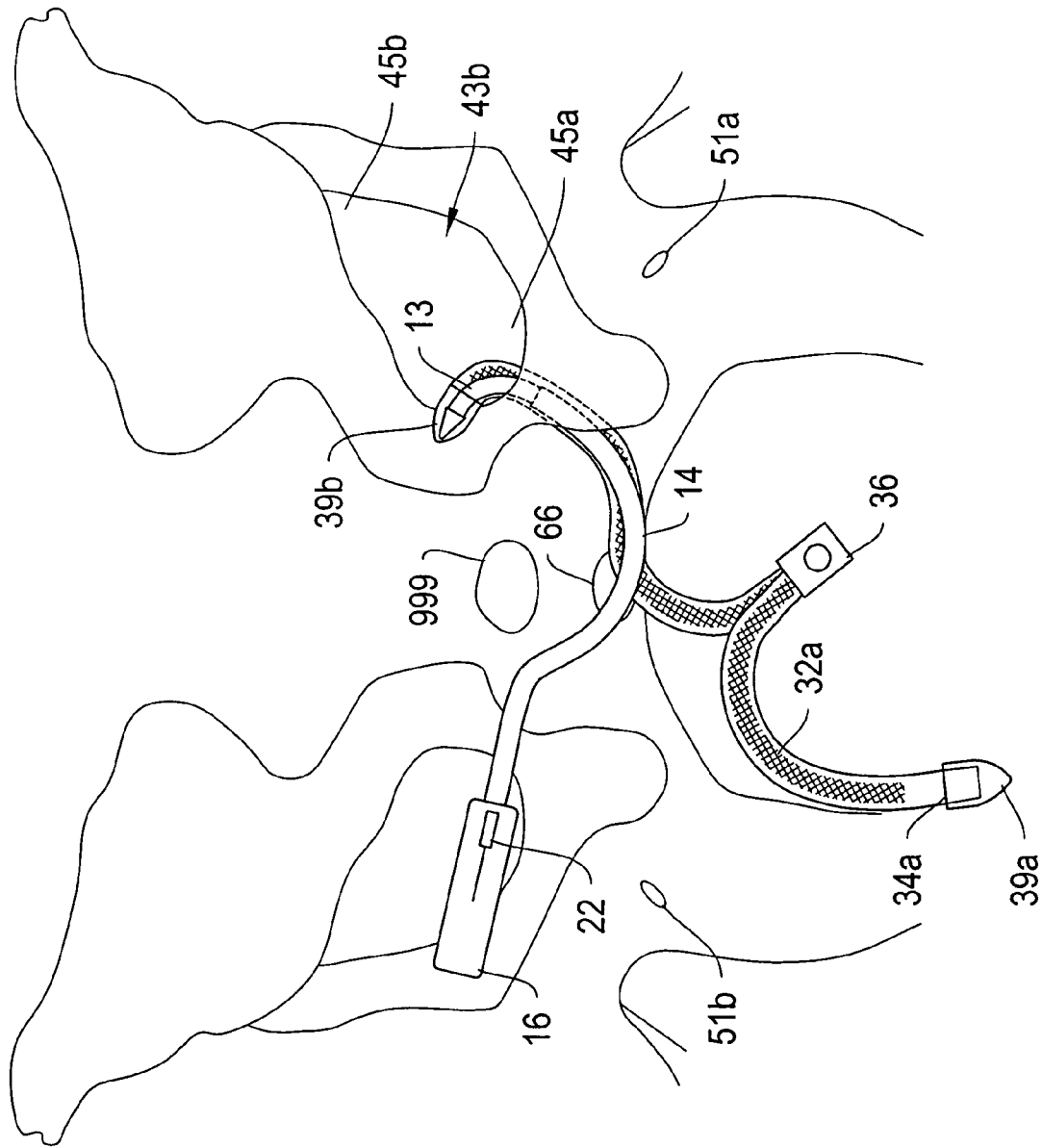
FIG. 5 depicts the illustrative trans-obturator approach of FIG. 4, after passage through the obturator foramen and with the interior shaft in the extended position of FIG. 2.

FIGS. 4 and 5 show an illustrative inside-out trans-obturator approach for delivering an implant, such as a sling or sling assembly, to an anatomical site in the body of a patient by using a delivery device such as those described herein. These and other approaches, such as for example suprapubic, pre-pubic and transvaginal approaches, are disclosed in the patents and patent applications cited herein. All operative combinations between the disclosed delivery device and these alternative procedures are contemplated. The delivery device described above may be employed to create a passage through body tissue, for example, from the inferior pubic ramus through the obturator foramen to the vagina or the reverse according to the methodologies described herein.

In the trans-obturator approach depicted in FIGS. 4 and 5, the smaller radius r of the shaft 12 allows the sling to be inserted in an "inside-out" approach while minimizing damage to sensitive vascular and nerve tissue near the posterior region of the patient's obturator foreman. In general, the operator inserts the sling assembly 30 through a vaginal incision and through the obturator foramen 43b and 43a such that the sling assembly 30 follows a path through the anterior regions (e.g., region 45a) of the obturator foramen 43a and 43b, which regions are surrounded by considerably less vascular and nerve tissue than are the posterior regions (e.g., region 45b) of the foramen 43a and 43b.

More particularly, in a first step, the operator provides a delivery device 10 with the shaft 12 retracted inside the guide tube 14 and attached to a sling assembly 30 through a connector, such as dilator tube 39b (but may also be it soft tissue anchor). The operator then associates the connector with the shaft 12 (e.g., slides the dilator tube 39b depicted in FIG. 3A over the tip 13 of the shaft 12) and the distal end 20 of the guide tube 14. The operator makes a vaginal incision 66, inserts the distal end 20 of the guide tube 14 of the delivery device 10 into the vaginal incision 66, and pushes the delivery device 10 and attached sling assembly 30 from the vaginal incision 66 to an obturator foramen 43b (or 43a) along the anterior region of the foramen 43b (or 43a). The operator then pushes the guide tube 14 with the attached connector (e.g., dilator tube 39b) through the obturators foramen 43b.

After the obturator membrane is pierced by the tip 13 of shaft 12, which is still retracted toward or inside the guide tube 14, the operator extends the shaft 12 by operating actuator 22 on handle 16 (FIG. 2). The shaft 12 may then be disengaged from the sling assembly 30 and retracted through the vaginal incision 66, leaving the sling assembly 30 anchored through the anterior region of the obturator foramen near the pubic ramus. In this approach, the end portions 32a and 32b of sling 32 connector may be a soft tissue anchor attached to the sling and anchoring the sling directly in the tissue located in or behind the obturator membrane, i.e. away from the vaginal incision. In alternative implementations, the shaft 12 may be further tunneled through the patient's tissues toward the patient's groin to the region of an ischiopubic incision 51b (or 51a). The shaft 12 may be delivered through the incision 51b and surface of the groin, and the connectors and sling assembly clipped so the assembly 30 lies flush with or is sutured to the patient's dermal tissue. The smaller radius r of the shaft 12 allows this extension to proceed through a region of the patient's tissues located behind, but near the anterior region of the obturator foramen, thus avoiding much of the sensitive vasculature and nerve tissue located near the posterior region of the obturator foramen. In alternative embodiments the process is then repeated with the same or a second delivery device on the contralateral side of the body with the second connector (e.g., soft tissue anchor or dilator tube 39a) of the sling assembly. In an alternative approach, the operator extends the shaft 12 to an anatomical position in front of the obturator membrane without piercing the membrane by the tip 13 of the shaft 12. In this approach, the sling 32 is configured with soft tissue anchor end portions (e.g., portions 32a and 32b) for anchoring into the soft tissue in front of the membrane.

Sling assemblies with soft tissue anchors and devices and methods for applying slings with soft tissue anchors are disclosed, for example, in commonly assigned U.S. patent application Ser. No. 11/400,111, filed Apr. 6, 2006 and entitled "Systems, Devices and Methods for Treating Pelvic Floor Disorders," U.S. patent application Ser. No. 11/399,913, filed Apr. 6, 2006 and entitled "Systems, Devices and Methods for Suburethral Support," and Ser. No. 11/152,898, filed Jun. 14, 2005 and entitled "Systems, Methods and Devices Relating to Implantable Supportive Slings," the contents of each of which are incorporated by reference herein in their entirety.

Optionally, a cystoscopy is performed with the delivery device(s) in place, prior to withdrawal of the delivery device (s) to verify integrity of the bladder. Cystoscopy could also be performed, as desired, after each placement of a delivery device on a side of the body. Alternatively, cystoscopy could be performed after withdrawal of the delivery devices.

In certain exemplary embodiments, as described more fully below, during the process of extending the shaft 12, the operator may change the temperature of the shaft, or at least the temperature of the shaft portion made of the shape memory material, to change the curvature of the extended portion of shaft 12. The extension of the shaft 12 enables the tip 13 to track close to the posterior surface of the ishiopubic bone, due to the smaller radius r of the extended shaft 12, thereby minimizing disturbance of surrounding tissue.

In an alternative "outside-in" approach, the delivery device 10 is inserted from an ishiopubic incision 51a (or 51b) through the obturator foramen 43a (or 43b) towards a vaginal incision 66. The operator palpates the obturator foramen to confirm that the anterior region receives the distal end 20 of guide tube 14. The shaft 12 is then extended and assumes a different curvature as described above.

Figure 6:
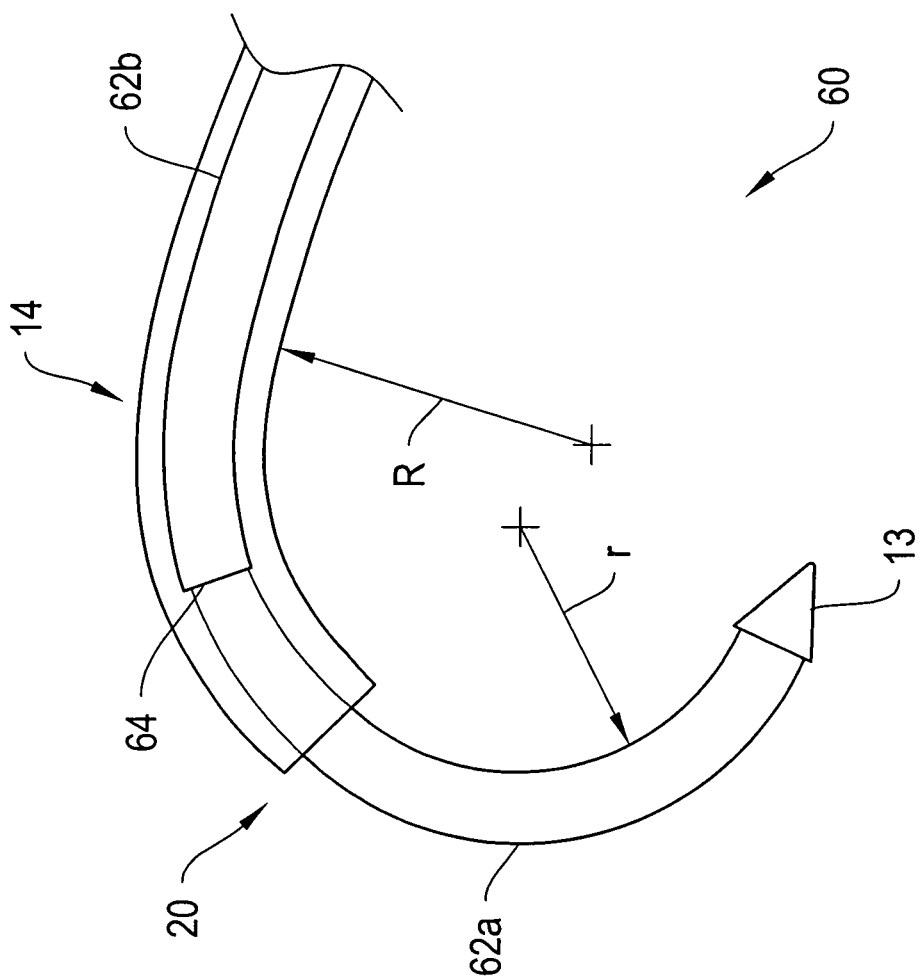
FIG. 6 depicts one embodiment of the distal portion of an interior shaft, shown in an extended position.

In certain exemplary embodiments, as illustrated in FIG. 6, the change in the radius of shaft 12 from the larger radius R (or curvature) inside the guide tube 14 to the smaller radius (or curvature) outside the guide tube 14 is effected by configuring the shaft 12 to have a pre-shaped distal section 62a with a pre-shaped radius of curvature r at its distal end. The pre-shaped distal section 62a assumes the shape of the tube 14 with radius R when forced into the tube 14 but, upon expulsion from the tube 14, reverts to its pre-biased shape with radius of curvature r. In certain embodiments the shaft is configured from a single section of material, such as a long piece of thin Nitinol. As indicated in FIG. 6, the shaft 12 may be made in two or more sections 62a and 62b, with the extendible section 62a made from a shape memory material, and the guided section 62b made of, for example, a flexible material. The sections 62a and 62b can be joined at connecting point 64, for example, by welding, brazing or with an adhesive.

Figure 7:
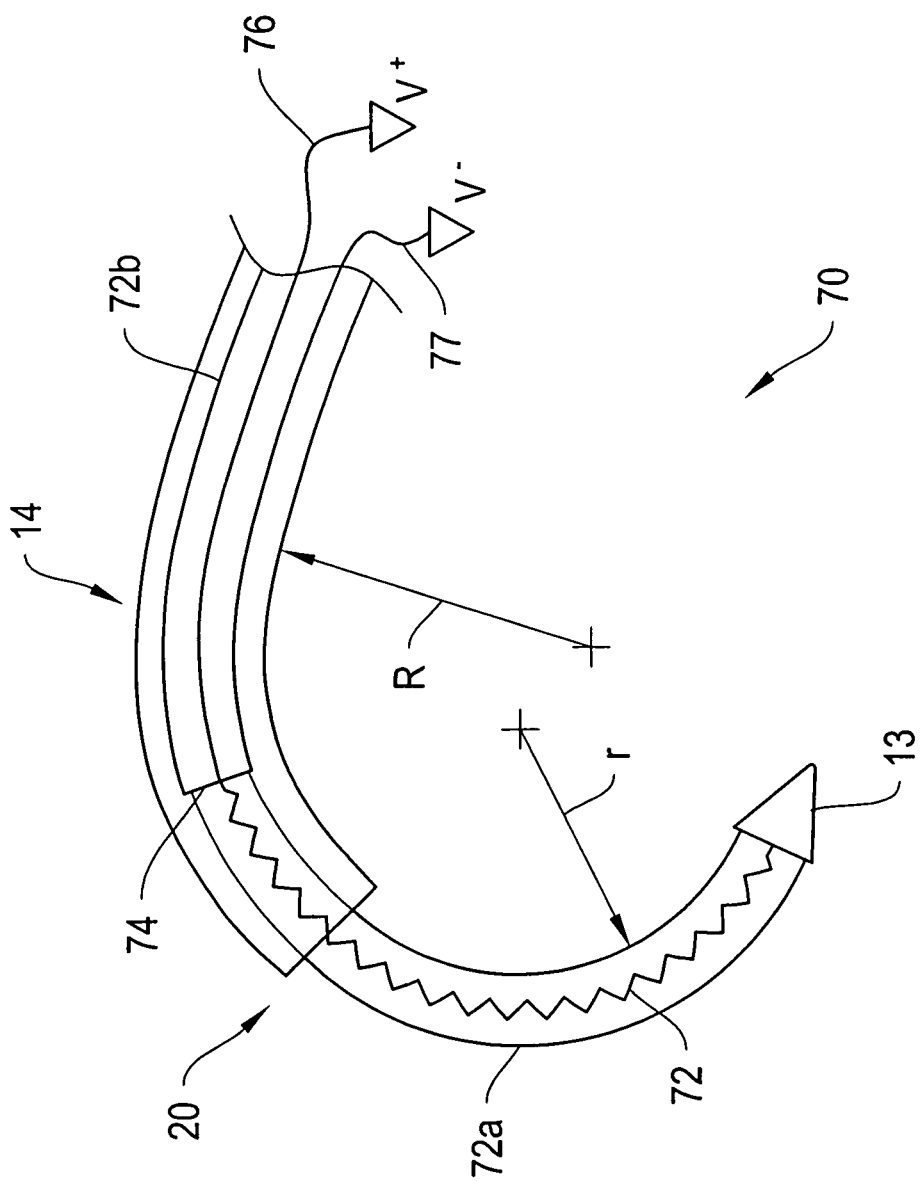
FIG. 7 depicts another embodiment of the distal portion of an interior shaft with a heating/cooling element disposed inside the shaft.

As noted above, in certain embodiments the change in radius can be effected by a change in the temperature of the shaft 12 after the shaft is expelled from the tube 14. The temperature changes from start to finish of a transformation are small and can be controlled to within a degree or two if necessary. FIG. 7 shows an exemplary configuration that includes a shaft temperature control system for changing the shape of the shaft 12, which can also be made of a distal shaft section 72a extendible from the guide tube 14 and a proximate shaft section 72b that remains inside the guide tube 14. In particular, a distal portion of the guide tube 14 is shown with a hollow shaft 12 and a heating or cooling element 72 placed inside the shaft 12, in the illustrated embodiment inside extendible shaft section 72a. Illustratively, the heating/ cooling element 72 raises/lowers the temperature of the shaft 12 from the patient's body temperature, for example, 38° C., to a slightly higher temperature, e.g., 40-50° C., when the shaft is extended, or maintains the shaft at a temperature below the patient's body temperature when the shaft 12 is retracted. Heating and cooling can be combined for attaining a wider temperature differential.

The heating and cooling element 62 may be energized by applying an electric current through conductors 76 and 77. One of the conductors 77 can be the shaft 12, or the shaft sections 72a, 72b. The temperature changes are large enough to effect the shape transformation but too small to cause discomfort in the patient. The aforementioned temperature range is merely exemplary, as the properties of Nitinol can be modified to a great extent by changes in alloy composition, mechanical working, and heat treatment. The temperature of the guide tube 14 or shaft 12 may also be changed by delivering electromagnetic, optical or chemical energy to the guide tube 14 or shaft 12. For example, the shaft 12 may include a passageway for receiving heated or cooled fluid to bring the shaft to temperatures that cover both the austenitic and the martensitic phase of Nitinol.

Without limitation, examples of slings, sling assemblies, delivery devices and implantation approaches that may be employed with respect to some features of illustrative embodiments of the invention are disclosed in U.S. Pat. No. 6,666,817, entitled "Expandable surgical implants and methods of using them," U.S. Pat. No. 6,669,706, entitled "Thin soft tissue surgical support mesh," U.S. Pat. No. 6,375,662, entitled "Thin soft tissue surgical support mesh," U.S. Pat. No. 6,042,592, entitled "Thin soft tissue surgical support mesh," U.S. Pat. No. 6,752,814, entitled "Devices for minimally invasive pelvic surgery," U.S. patent application Ser. No. 10/774,826, entitled "Devices for minimally invasive pelvic surgery," U.S. patent application Ser. No. 10/093,398, entitled "System for implanting an implant and method thereof," U.S. patent application Ser. No. 10/093,498, entitled "System for implanting an implant and method thereof," U.S. patent application Ser. No. 10/093,371, entitled "System for implanting an implant and method thereof," U.S. Pat. No. 6,936,052, entitled "System for implanting an implant and method thereof," U.S. patent application Ser. No. 10/093,450, entitled "System for implanting an implant and method thereof," U.S. patent application Ser. No. 10/094,352, entitled "System for implanting an implant and method thereof," U.S. patent application Ser. No. 10/631,364, entitled "Bioabsorbable casing for surgical sling assembly," U.S. patent application Ser. No. 10/641,376, entitled "Spacer for sling delivery system," U.S. patent application Ser. No. 10/641,487, entitled "Systems, methods and devices relating to delivery of medical implants," U.S. patent application Ser. No. 10/642,395, entitled "Systems, methods and devices relating to delivery of medical implants," U.S. patent application Ser. No. 10/642,397, entitled "Systems, methods and devices relating to delivery of medical implants," U.S. patent application Ser. No. 10/832,653, entitled "Systems and methods for sling delivery and placement," the entire contents of all of which are incorporated herein by reference.

Variations, modifications, and other implementations of what is described may be employed without departing from the spirit and the scope of the invention. More specifically, any of the method, system and device features described above or incorporated by reference may be combined with any other suitable method, system or device features disclosed herein or incorporated by reference, and is within the scope of the contemplated inventions.

What is claimed is:

1. A device for delivering an implant to a patient's pelvic region comprising:
    a guide tube with a proximal end, a distal end and a first radius of curvature;
    a shaft slidingly interfitted in the guide tube with a proximal end and a distal end, the shaft adapted to extend out from a terminus of the distal end of the guide tube in a first position and retract into the distal end of the guide tube in a second position, the shaft having a lumen defined therein, at least the distal end of the shaft including a shape memory material;
    at least one of a heating element and a cooling element disposed in the lumen in at least the distal end of the shaft, the at least one of the heating element and the cooling element configured to be energized based on whether the shaft is in the first position or the second position, wherein the heating element is energized to increase a temperature of the shape memory material above a phase transition temperature of the shape memory material when at least the distal end of the shaft is extended to protrude from the distal end of the guide tube;
    a handle secured to the proximal end of the guide tube; and
    an actuator slidably disposed on or in the handle for causing the distal end of the shaft to protrude from and be retracted into the guide tube,
    wherein the shaft has a radius of curvature substantially equal to the first radius of curvature when retracted in the guide tube, and wherein at least the distal end of the shaft assumes a second radius of curvature different from the first radius of curvature of the guide tube, when the distal end of the shaft extends from the guide tube.

2. The device of claim 1, wherein at least the distal end of the shaft is preformed with the second radius of curvature before being inserted in the guide tube.

3. The device of claim 1, wherein the shape memory material comprises a nickel titanium alloy.

4. The device of claim 1, wherein the phase transition temperature is in a range of a body temperature of a mammal.

5. The device of claim 1, further comprising a connector adapted to attach to a sling assembly, the connector attached to or integrally formed with the distal end of the shaft.

6. The device of claim 1, wherein the cooling element is energized to decrease a temperature of the shape memory material below the phase transition temperature of the shape memory material when at least the distal end of the shaft is retracted toward the distal end of the guide tube.

7. The device of claim 1, wherein the second radius of curvature of the distal end of the shaft is smaller than the first radius of curvature of the guide tube.

8. A sling delivery assembly comprising:
    a delivery device having:
        a guide tube with a proximal end and a distal end, the distal end of the guide tube having a first radius of curvature;
        a shaft slidingly interfitted in the guide tube and having a proximal end and a distal end, the distal end of the shaft having a radius of curvature substantially identical to the first radius of curvature while inside the guide tube and being adapted to protrude from the distal end of the guide tube with a second radius of curvature different from the first radius of curvature, the shaft having a lumen defined therein; at least one of a heating element and a cooling element disposed in the lumen in at least the distal end of the shaft, the at least one of the heating element and the cooling element configured to be energized based on whether the shaft is protruded from the guide tube or inside the guide tube;
        a first connector attached to or integrally formed with the distal end of the shaft;
        a handle secured to the proximal end of the guide tube; and
        an actuator disposed on or in the handle for causing the distal end of the shaft to protrude from and be retracted into the distal end of the guide tube; and
    a sling assembly having a proximal end and a distal end, and a second connector attached to or integrally formed with the distal end of the sling assembly.

9. The assembly of claim 8, wherein the delivery device further comprises a dilator tip or tissue dissector disposed on the distal end of the shaft.

10. The assembly of claim 8, wherein the second connector of the sling assembly is formed as a dilator.

11. The assembly of claim 8, wherein the distal end of the shaft includes a shape memory material.

12. The assembly of claim 11 wherein the heating element is energized to increase a temperature of the shape memory material above a phase transition temperature of the shape memory material when at least the distal end of the shaft is extended to protrude from the distal end of the guide tube.

13. The assembly of claim 11, wherein the cooling element is energized to decrease a temperature of the shape memory material below a phase transition temperature of the shape memory material when at least the distal end of the shaft is retracted inside the distal end of the guide tube.

14. The assembly of claim 11, wherein the shape memory material comprises a nickel titanium alloy.

15. The assembly of claim 11, wherein the shape memory material has a phase transition temperature in a range of a body temperature of a mammal.

16. The assembly of claim 8, wherein the second radius of curvature of the distal end of the shaft is smaller than the first radius of curvature of the guide tube.

17. A method of implanting a surgical sling into a pelvic region of a patient, the method comprising:
    inserting a delivery device coupled to a sling assembly with a surgical sling through an incision of a patient;
    extending a shaft portion from a distal end of the delivery device to navigate around a bodily structure, at least a distal end of the extended shaft portion assuming a curvature different from a curvature of the distal end of the delivery device wherein the shaft portion is extended by moving an actuator disposed on or in a handle of the delivery device, the actuator configured to slidably cause the distal end of the shaft portion to protrude from and be retracted into the distal end of the delivery device; and at least one of heating at least the distal end of the shaft portion when the shaft portion is extended, or cooling at least the distal end of the shaft portion when the shaft portion is retracted.

18. The method of claim 17, further comprising retracting the extended shaft portion after placement of the surgical sling, with the distal end of the retracted shaft portion conforming to the curvature of the distal end of the delivery device.

19. The method of claim 17, further comprising advancing the delivery device to a vicinity of an obturator foramen of the patient.

20. The method of claim 19, wherein advancing the delivery device includes penetrating the obturator foramen and extending the shaft portion around and in close proximity to an ischiopubic ramus of the patient.

* * * * *